(12) United States Patent
Anderson et al.

(10) Patent No.: US 10,265,113 B2
(45) Date of Patent: Apr. 23, 2019

(54) AVULSION FRACTION FIXATION CONSTRUCT

(71) Applicant: Biomet Manufacturing, LLC, Warsaw, IN (US)

(72) Inventors: David M. Anderson, Winona Lake, IN (US); Gregory J. Denham, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 420 days.

(21) Appl. No.: 14/991,914

(22) Filed: Jan. 9, 2016

(65) Prior Publication Data

US 2016/0199115 A1 Jul. 14, 2016

Related U.S. Application Data

(60) Provisional application No. 62/101,720, filed on Jan. 9, 2015, provisional application No. 62/257,423, filed on Nov. 19, 2015.

(51) Int. Cl.
*A61B 17/88* (2006.01)
*A61B 17/04* (2006.01)
(Continued)

(52) U.S. Cl.
CPC ...... *A61B 17/8869* (2013.01); *A61B 17/0401* (2013.01); *A61B 17/06166* (2013.01);
(Continued)

(58) Field of Classification Search
CPC ..... A61B 17/56; A61B 17/88; A61B 17/8869; A61B 17/0401; A61B 17/8897;
(Continued)

(56) References Cited

U.S. PATENT DOCUMENTS 2,572,650 A 10/1951 Walter
5,474,554 A 12/1995 Ku
(Continued)

FOREIGN PATENT DOCUMENTS

EP 2572650 A1 3/2013
EP 2676612 A2 12/2013
(Continued)

OTHER PUBLICATIONS

"U.S. Appl. No. 15/355,714, Preliminary Amendment filed Nov. 23, 2016", 3 pgs.
(Continued)

*Primary Examiner* — Victor Nguyen
(74) *Attorney, Agent, or Firm* — Schwegman Lundberg & Woessner, P.A.

(57) ABSTRACT

A method of fixing a proximal bone mass to a distal bone mass can include driving a guide wire through the proximal bone mass and the distal bone mass to define a path through the proximal bone mass and the distal bone mass. The method can include inserting a suture from the proximal bone mass into the distal bone mass along the path defined by the guide wire and fixing the suture to the distal bone mass. The method can further include tensioning the suture to draw the distal bone mass against the proximal bone mass.

16 Claims, 12 Drawing Sheets

(51) Int. Cl.
*A61B 17/17* (2006.01)
*A61B 17/06* (2006.01)

(52) U.S. Cl.
CPC ...... *A61B 17/1796* (2013.01); *A61B 17/8897* (2013.01); *A61B 2017/0441* (2013.01); *A61B 2017/0445* (2013.01); *A61B 2017/0446* (2013.01)

(58) Field of Classification Search
CPC ............ A61B 17/0487; A61B 17/1796; A61B 2017/0441; A61B 2017/0445; A61B 2014/0446; A61B 2017/0409; A61B 2014/0414
See application file for complete search history.

(56) References Cited

U.S. PATENT DOCUMENTS

| | | | |
|---|---|---|---|
| 2006/0276841 A1* | 12/2006 | Barbieri | A61B 17/0401 606/232 |
| 2008/0312689 A1 | 12/2008 | Denham et al. | |
| 2009/0306711 A1* | 12/2009 | Stone | A61B 17/0401 606/232 |
| 2014/0316460 A1 | 10/2014 | Graul et al. | |
| 2017/0172561 A1 | 6/2017 | Denham | |

FOREIGN PATENT DOCUMENTS

| | | |
|---|---|---|
| WO | WO-2016112362 A1 | 7/2016 |
| WO | 2017087812 | 5/2017 |

OTHER PUBLICATIONS

"International Application Serial No. PCT/US2016/012762, International Search Report dated Apr. 1, 2016", 5 pgs.

"International Application Serial No. PCT/US2016/012762, Written Opinion dated Apr. 1, 2016", 7 pgs.

"International Application Serial No. PCT/US2016/062791, International Search Report dated Feb. 22, 2017", 4 pgs.

"International Application Serial No. PCT/US2016/062791, Written Opinion dated Feb. 22, 2017", 6 pgs.

"International Application Serial No. PCT/US2016/012762, International Preliminary Report on Patentability dated Jul. 20, 2017", 9 pgs.

"U.S. Appl. No. 15/355,714, Non Final Office Action dated May 3, 2018", 14 pgs.

"European Application Serial No. 16702250.8, Response filed Mar. 19, 2018 to Office Action dated Sep. 7, 2017", 18 pgs.

"International Application Serial No. PCT/US2016/062791, International Preliminary Report on Patentability dated May 31, 2018", 8 pgs.

* cited by examiner

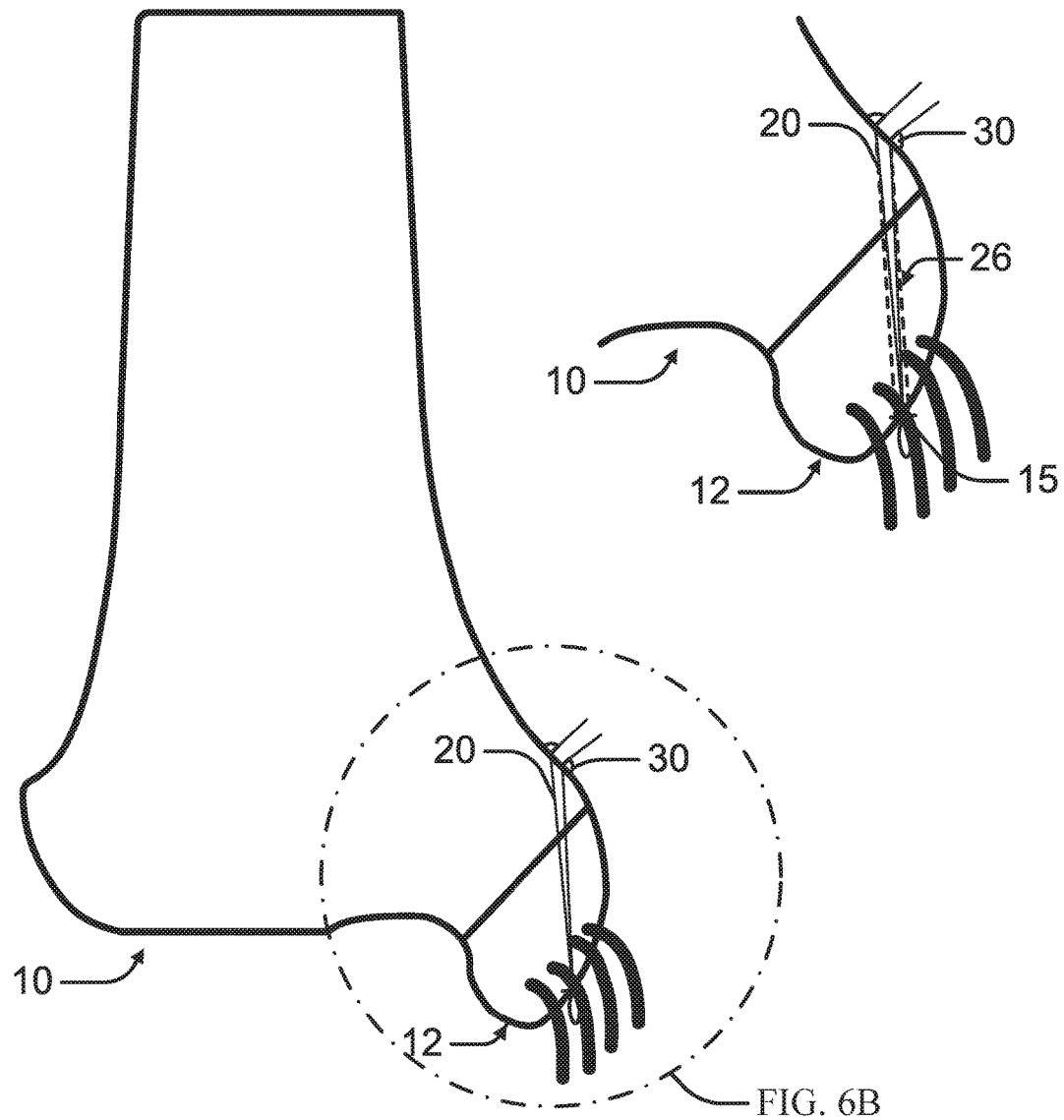

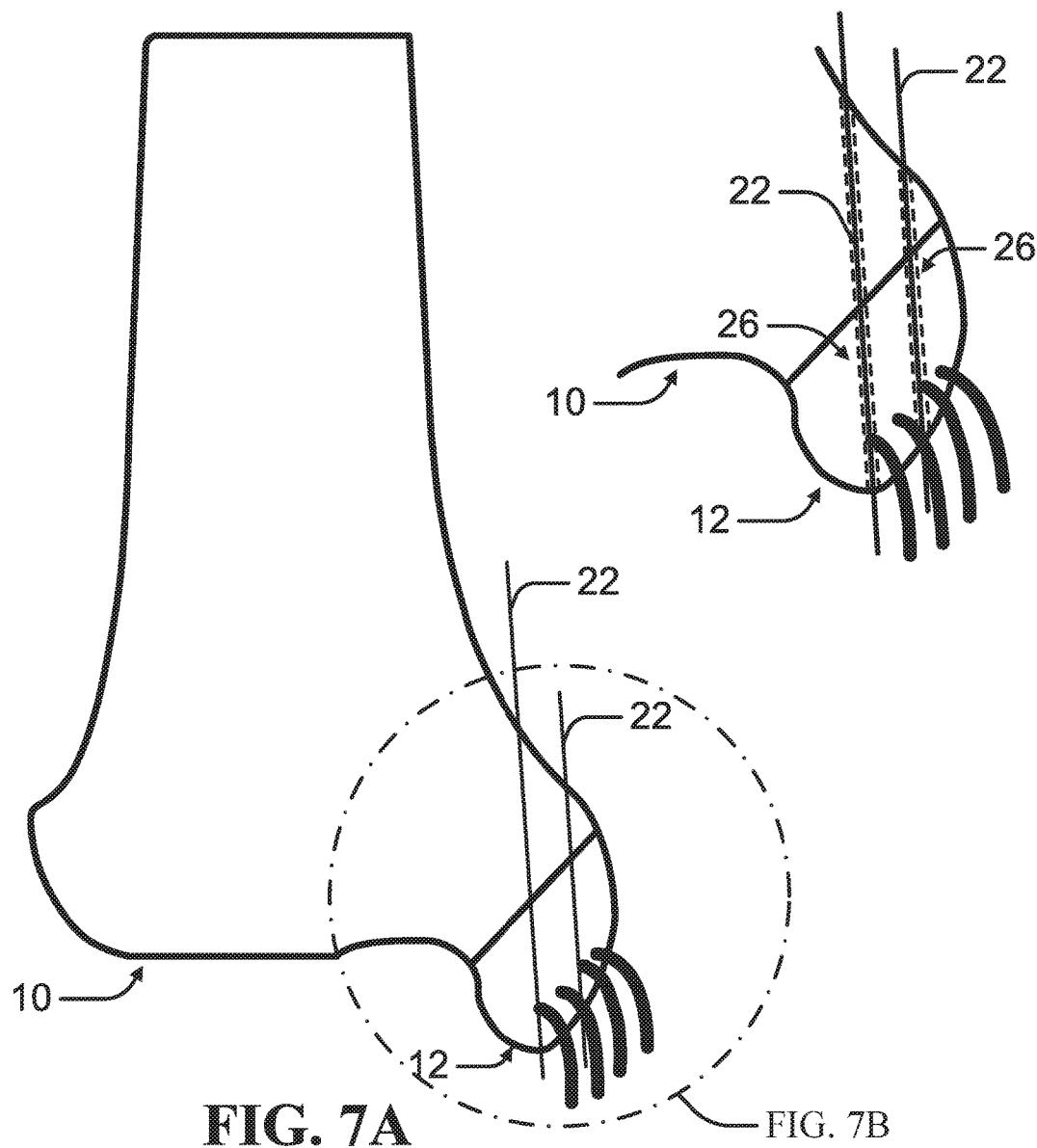

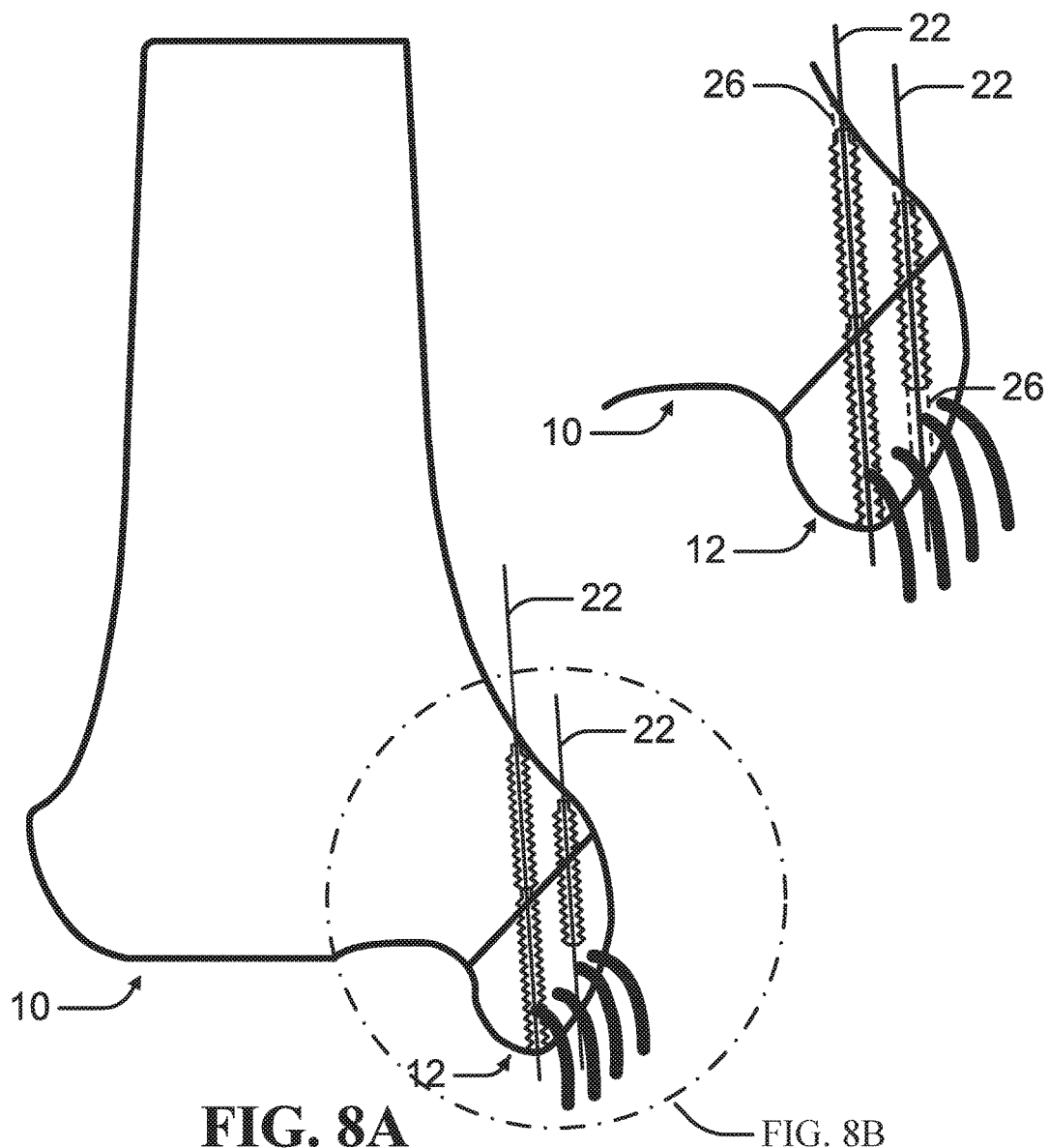

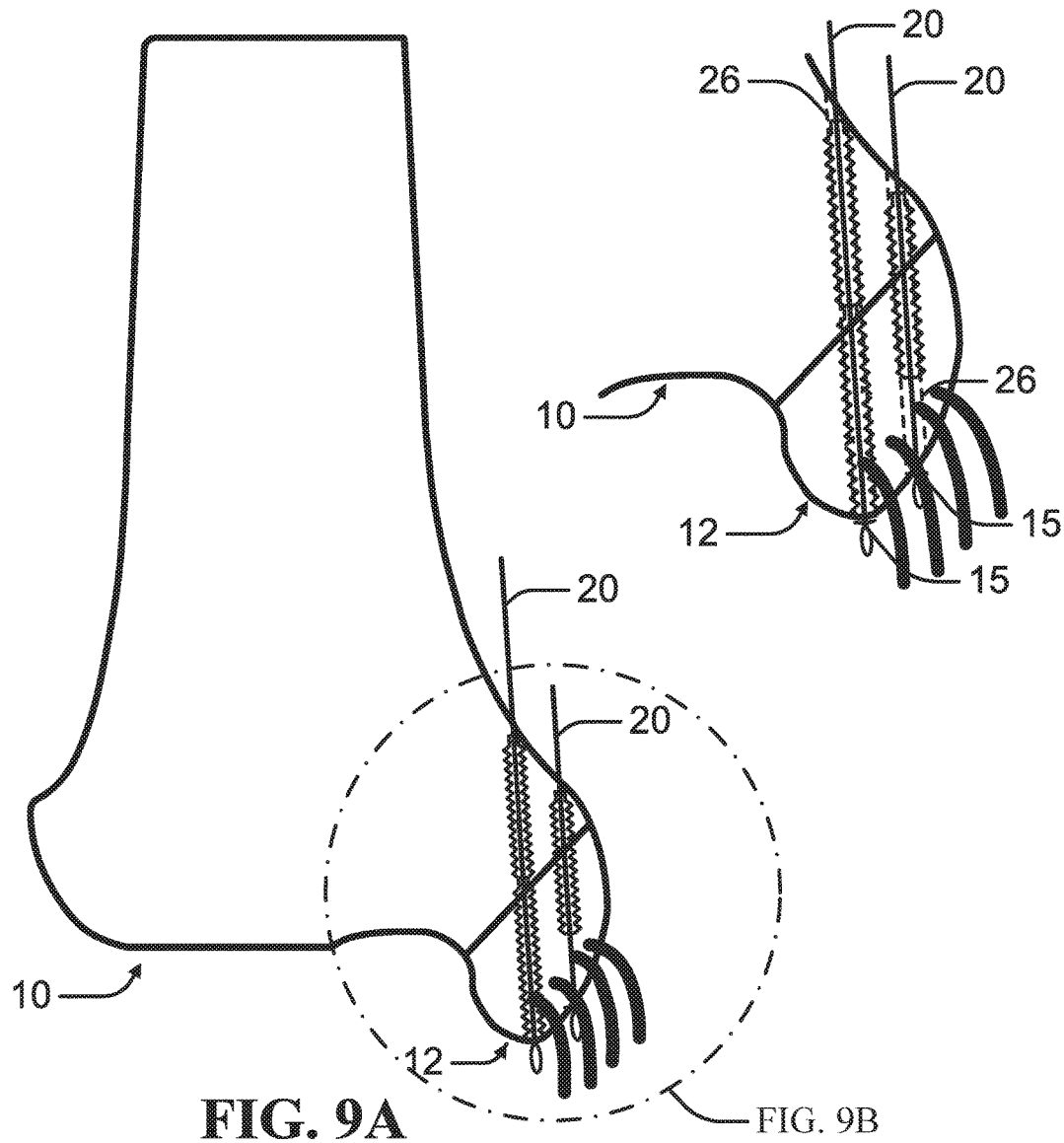

AVULSION FRACTION FIXATION CONSTRUCT

CLAIM OF PRIORITY

This patent application claims the benefit of priority, under 35 U.S.C. Section 119(e), to David Anderson, U.S. Provisional Patent Application Ser. No. 62/101,720, entitled "AVULSION FRACTION FIXATION CONSTRUCT," filed on Jan. 9, 2015 and Gregory J. Denham, U.S. Provisional Patent Application Ser. No. 62/257,423, entitled "HYBRID SUTURE ANCHOR", filed Nov. 19, 2015, each of which is hereby incorporated by reference herein in its entirety.

TECHNICAL FIELD

This document pertains generally, but not by way of limitation, to a fixation system and related methods for securing a bone fleck or flake to the main bone mass created by an avulsion fracture.

BACKGROUND

In an avulsion fracture, a bone fleck or flake fractures from the main mass of the bone due to trauma to the bone. Avulsion fractures typically occur at joints where soft tissue, such as ligaments, is attached to protruding portions of the bone. The ligament can contract following the fracture and pull the fleck away from main bone mass. In reconstructive surgery, the fleck is held against the main bone mass with one or more set screws until the fleck fuses to the main bone mass. Bore holes for each set screw can be drilled into the bone fleck and the main bone mass for setting the set screw into the bone. After the bone fleck has fused to the main bone mass, the screws are commonly removed to permit the bone to heal and close the boreholes.

A disadvantage of set screws is the sizing of the boreholes that must be drilled for positioning the set screws. The set screws are typically 3-4 mm in diameter requiring similarly sized boreholes. If the bone fleck is too thin or small, the bone fleck can fracture or break into smaller fragments during drilling of the boreholes. As a result, surgeons often select thicker portions of the bone fleck that are sufficiently thick to receive a set screw. While minimizing the risk of fracturing or breaking the bone fleck, the positioning of the set screw can be less desirable for providing appropriate compression of the bone fleck to the main bone mass.

OVERVIEW

The present inventors have recognized, among other things, that a problem to be solved can include using set screws for securing bone flecks or flakes to the main bone mass. In an example, the present subject matter can provide a solution to this problem, such as by driving a guide wire through the bone fleck and the main bone mass. A suture can be inserted along the guide wire through the either the bone fleck or the main bone mass and into the other of the bone fleck or the main bone mass. The suture can be secured to the distal bone fragment such that the suture can be tensioned to draw the bone fleck against the main bone mass. After fusing of the bone fleck to the main bone mass, the suture can be removed from the bone. In an example, the suture can be biodegradable material such that the suture degrades following fusing of the bone fleck to the main bone mass.

In an example, a drive-in screw can be driven in along the guide wire. The suture can include a nose portion that can be expanded by tensioning the suture. In this configuration, the drive-in screw can operate as a backstop facilitating expansion of the nose portion as the suture is tensioned. In an example, the drive-in screw is sized such that drive-in screw is positioned only in the main bone mass. In at least one example, the drive-in screw is sized such that the drive in screw extends between the main bone mass and the bone fleck.

In an example, boreholes are drilled through the bone fleck and the main bone mass along the path defined by the guide wire. The suture can be threaded through the borehole of either the bone fleck or the main bone mass and into the borehole to the other of the bone fleck or the main bone mass. The suture can be secured to the other of the bone fleck or the main bone mass such that the suture can tensioned to draw the bone fleck against the main bone mass. As the suture is not secured to the bone defining the boreholes, the suture boreholes can have substantially smaller diameters then that of screw boreholes. Similarly, the thinner suture boreholes allow the boreholes to be positioned in thinner portions of the bone fleck without fracturing or breaking the fleck, thereby appropriate compression of the bone fleck to the main bone mass.

In an example, the suture can have a nose portion that can be fed through the bore holes, where the suture can be tensioned to radially expand the nose portion to engage one of the bone fleck or the main bone mass. The suture can be further tensioned to draw the bone fleck against the main bone mass. In an example, the suture can also have a tail portion that frictionally engages an inner surface of the borehole such that nose portion can be pulled against the tail portion to facilitate expansion of the nose portion. The tail portion can be removed after expansion of the nose portion. In this configuration, the tail portion can be configured to sufficiently engage the inner surface to brace the nose portion as the suture is tensioned to expand the nose portion.

In an example, a method of fixing a proximal bone mass to a distal bone mass can include driving a guide wire through the proximal bone mass and the distal bone mass to define a path through the proximal bone mass and the distal bone mass; inserting a suture from the proximal bone mass into the distal bone mass along the path defined by the guide wire; fixing the suture to the distal bone mass; and tensioning the suture to draw the distal bone mass against the proximal bone mass. The method can further include drilling a drive-in screw into at least the proximal bone mass along the path defined by the guide wire.

In at least one example, the suture includes an expandable nose portion, wherein the method further includes tensioning the suture when the nose portion is positioned within the distal bone mass to expand the nose portion and fix the suture to the distal bone mass. The suture can also include a tail portion having engagement features engagable to a bone surface of at least one of the distal bone mass and proximal bone mass, wherein tensioning the suture draws the nose portion against the tail portion to facilitate expansion of the nose portion against the distal bone portion.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6A is a schematic diagram of securing of a suture fixed to a bone fleck according to an example of the present disclosure.

FIG. 6B is an enlarged view of the schematic diagram of the securing of the suture depicted in FIG. 6B.

FIG. 7A is a schematic diagram of insertion of at least two guide wires through a main bone mass and a bone fleck to define a path according to an example of the present disclosure.

FIG. 7B is an enlarged view of the schematic diagram of the insertion of at least two guide wires depicted in FIG. 7A.

FIG. 8A is a schematic diagram of insertion of drive-in screws along paths defined by at least two guide wires according to an example of the present disclosure.

FIG. 8B is an enlarged view of the schematic diagram of the insertion of the drive-in screws depicted in FIG. 8A.

FIG. 9A is a schematic diagram of insertion of sutures along paths defined by at least two guide wire according to an example of the present disclosure.

FIG. 9B is an enlarged view of schematic diagram of the insertion of the sutures depicted in FIG. 9A.

DETAILED DESCRIPTION

Figure 1:
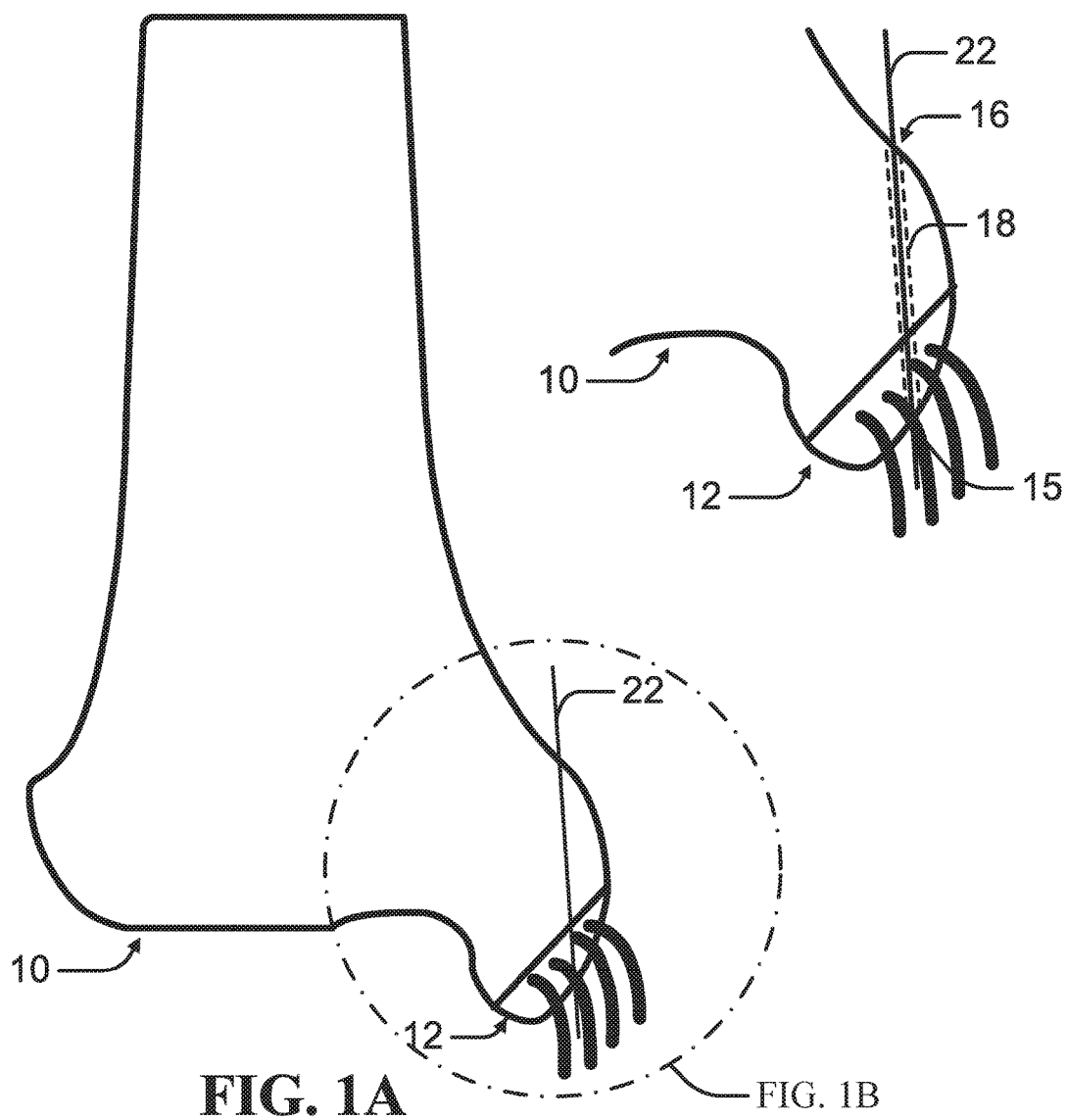
FIG. 1A is a schematic diagram of insertion of a guide wire according to an example of the present disclosure.
FIG. 1B is an enlarged view of the schematic diagram of the insertion of the guide wire depicted in FIG. 1A.
Figure 2:
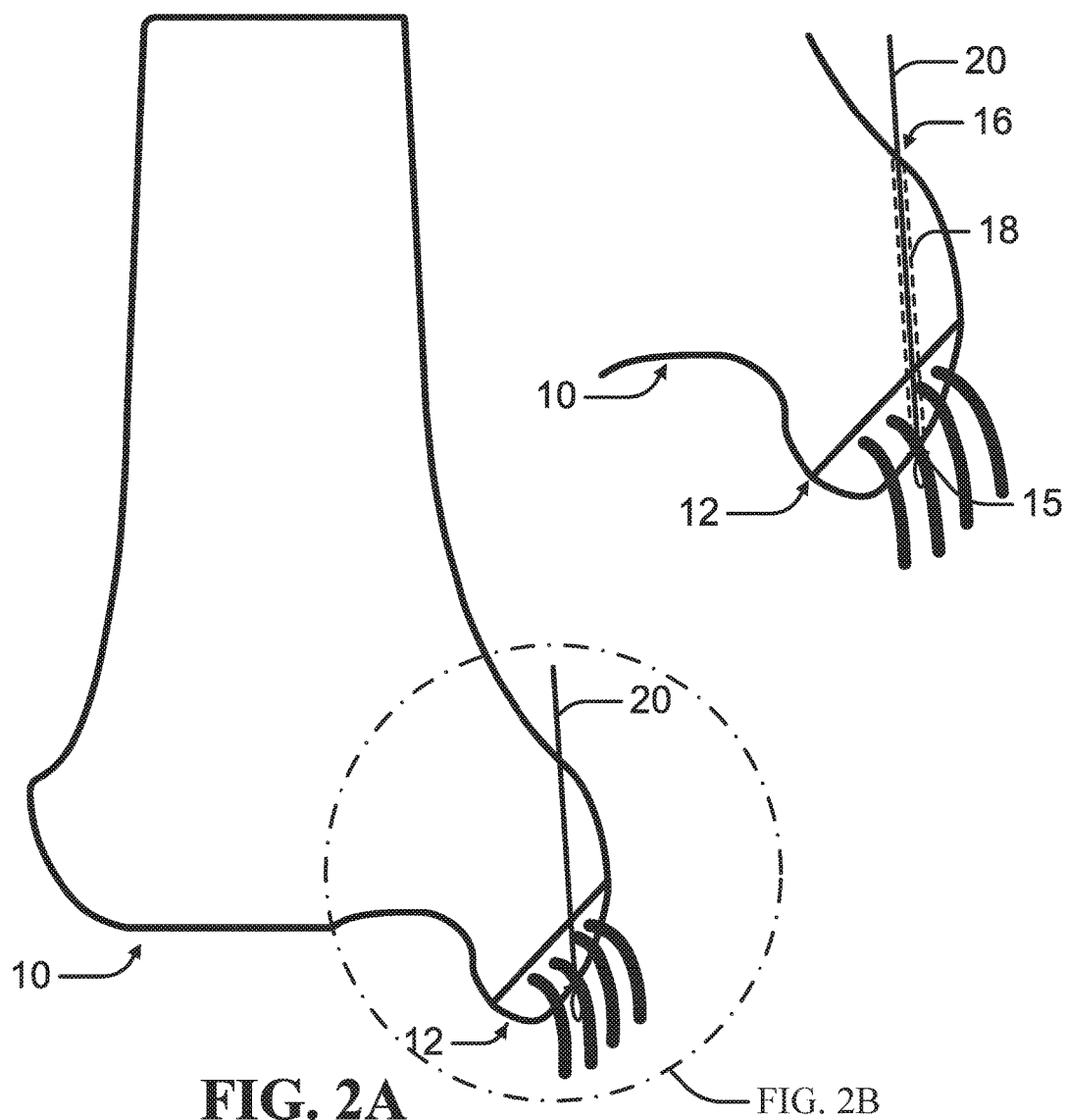
FIG. 2A is a schematic diagram of insertion of a suture along a path defined by a guide wire according to an example of the present disclosure.
FIG. 2B is an enlarged view of the schematic diagram of the insertion of the suture depicted in FIG. 2A.

As depicted in FIGS. 1A-2B, according to an example, a proximal bone mass 10 can be compressed against a distal bone mass 12 with a suture 20 to facilitate fusing of the proximal bone mass 10 to the distal bone mass 12. A guide wire 22, such as Kirschner wire or other elongated probe, can be driven through the proximal bone mass 10 and the distal bone mass 12 to define a path through the bone. In at least one example, the bone can be drilled to form a bore hole 16 defined by an inner surface 18. The suture 20 can be inserted through the path from the proximal bone mass 10 through the distal bone mass 12. The suture 20 can comprise materials such as braided filaments or fibers of biocompatible material, including natural and synthetic fibers, such as cotton, silk, polymer, polyester, polyethylene, thin wire, suture and other materials. The suture 20 can also be in the form of a flat tubular suture or a braided suture with or without a core.

In an example, the guide wire 22 can be inserted through the distal bone mass 12 to form a distal opening 15 in the distal bone mass 12. In this configuration, the suture 20 can extend through the distal opening 15 knotted or expanded to prevent withdrawal of the suture 20 when the suture 20 is tensioned. The suture 20 can be secured to the distal bone mass 12 such that the suture 20 can be tensioned to draw the distal bone mass 12 against the proximal bone mass 10.

As depicted in FIGS. 1-9, the proximal bone mass 10 is the main bone mass, while the distal bone mass 12 is the bone fleck. It is contemplated that insertion of the guide wire 22 and the suture 20 can be reversed such that the bone fleck is the proximal bone mass 10 and the main bone mass is the distal bone mass 12. Also, as depicted, the main bone mass is a tibia and the bone fleck is a portion of a protrusion from the tibia attached to a ligament. It is contemplated that bone to be repaired can be other bones that can be damaged by avulsion fracture.

Figure 3:
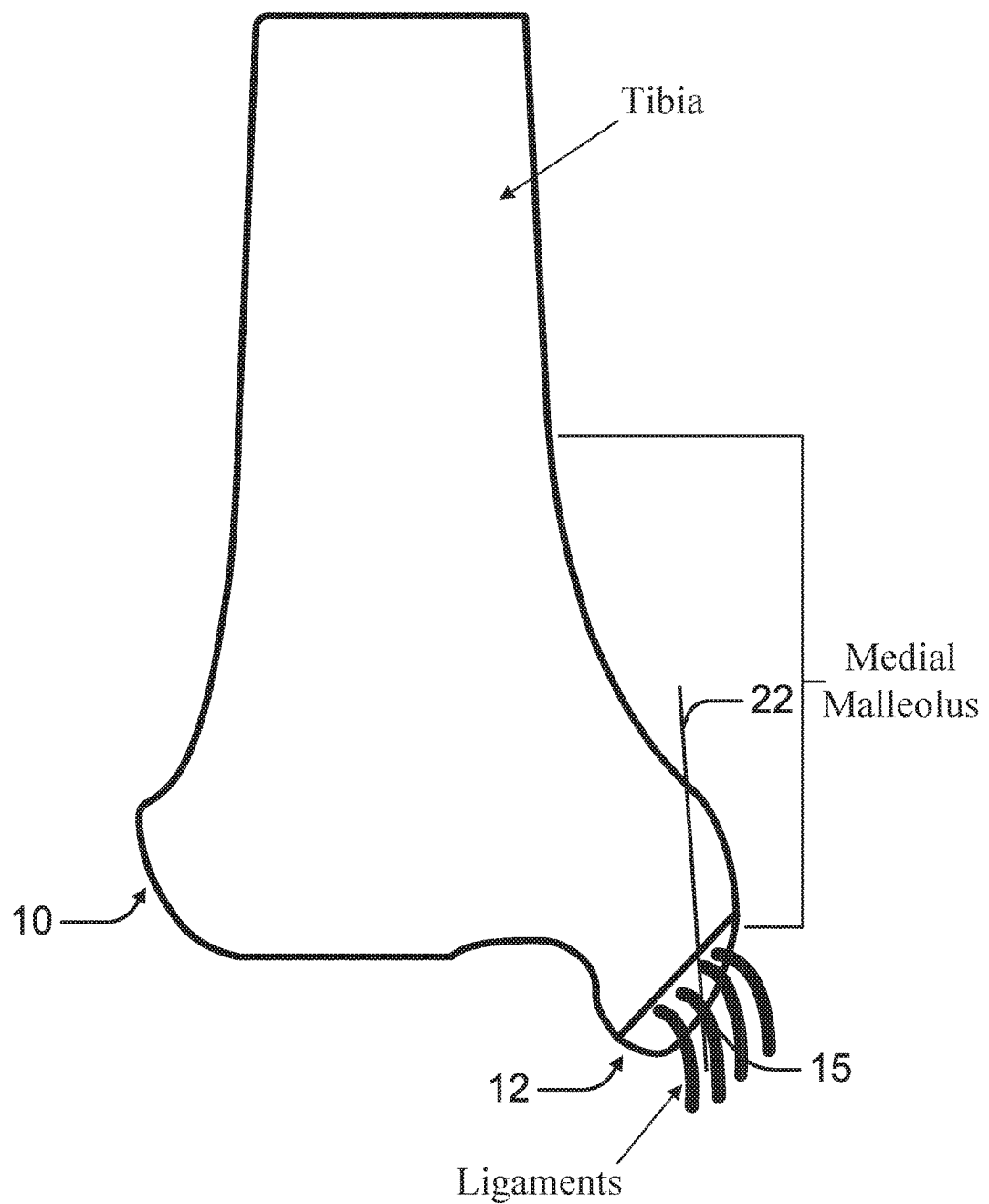
FIG. 3 is a schematic diagram of insertion of a guide wire through a main bone mass and a bone fleck to define a path according to an example of the present disclosure.

As depicted in FIG. 3, according to an example, a guide wire 22 is driven from the proximal bone mass 10 through the distal bone mass 12 to define a path through the bone. In an example, the guide wire 22 can be oriented to avoid or minimizing damage to any ligaments or soft tissue attached or proximate the distal bone mass 12. As depicted in FIGS. 7A-8B, at least two guide wires 22 can be driven from the proximal bone mass 10 through the distal bone mass 12, each defining a path through the bone.

Figures 4A, 4B:
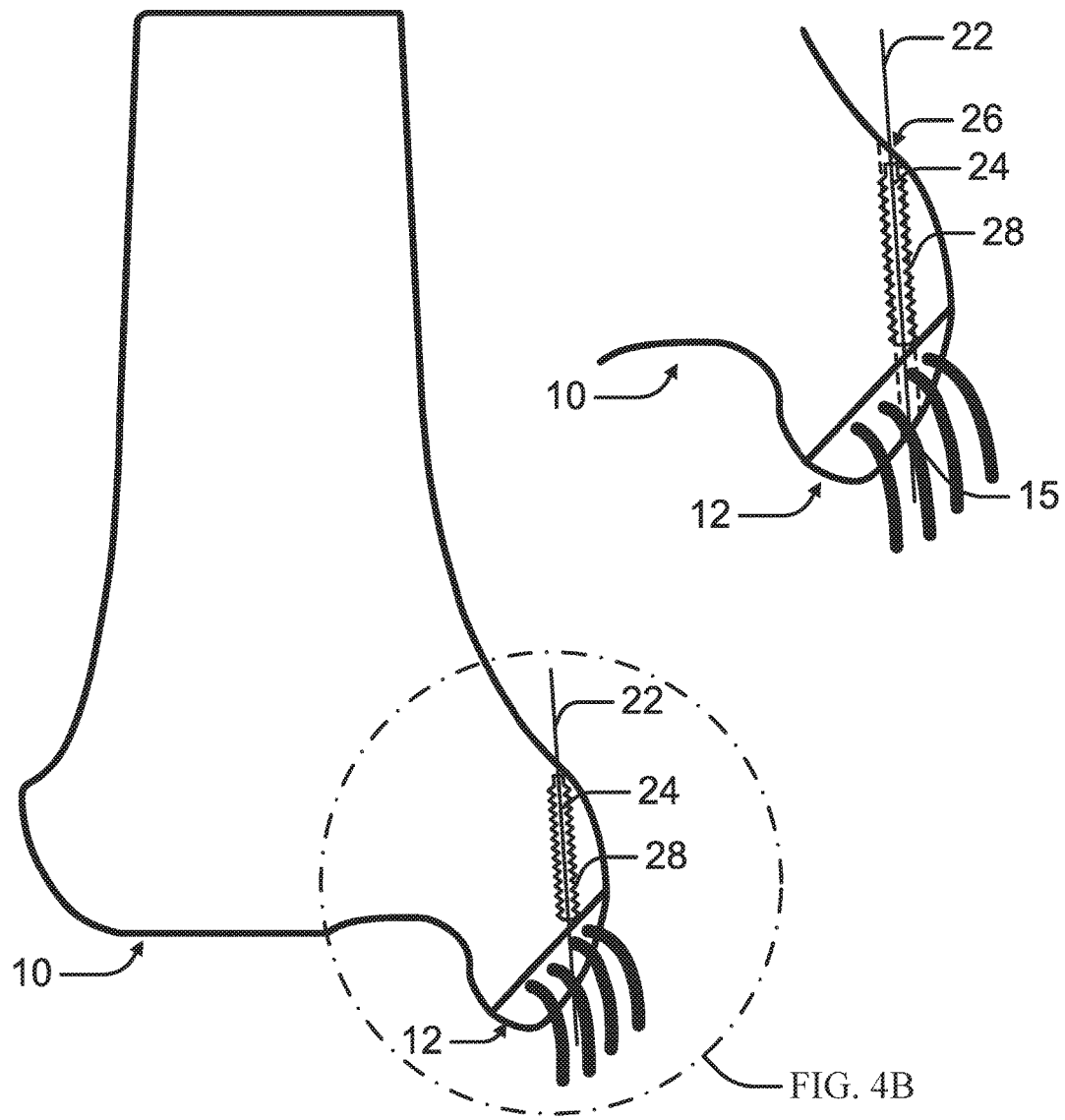
FIG. 4A is a schematic diagram of insertion of a drive-in screw along a path defined by a guide wire according to an example of the present disclosure.
FIG. 4B is an enlarged view of the schematic diagram of the insertion of the drive-in screw depicted in FIG. 4A.
Figure 5B:
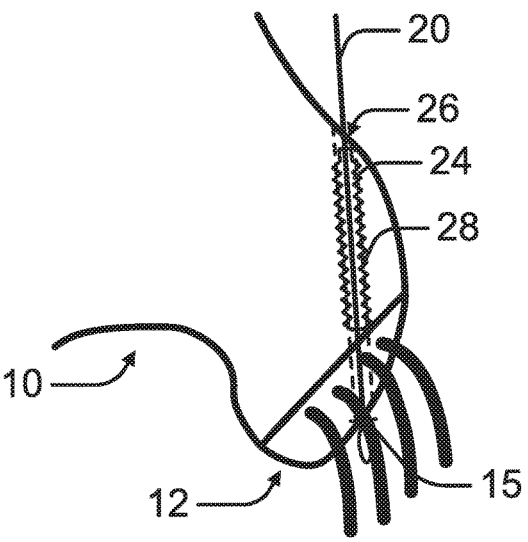
FIG. 5B is an enlarged view of the schematic diagram of the insertion of the suture depicted in FIG. 5A.
Figure 5A:
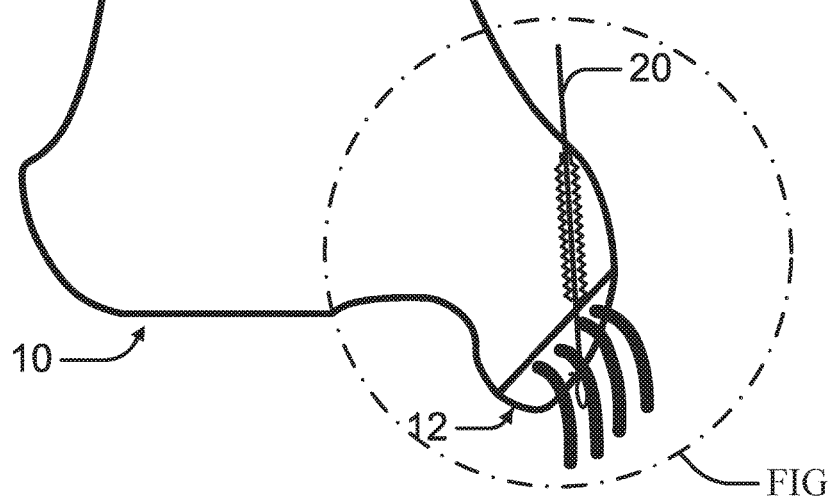
FIG. 5A is a schematic diagram of insertion of a suture along a path defined by a guide wire according to an example of the present disclosure.

As depicted in FIGS. 4A-B, a drive-in screw 24 can be driven at least into the proximal bone mass 10. Each drive-in screw 24 can define a channel 26 for receiving the suture 20. In at least one example, the drive-in screw 24 can be driven through the proximal bone mass 10 into the distal bone mass 12 as depicted in FIGS. 9A-B. Multiple drive-in screws 24 can be driven in end-to-end along the path defined by a single guide wire 22 as illustrated in FIGS. 8A-B. The drive-in screw 24 can include at least one engagement feature 28 engagable to the bone surrounding the path defined by the guide wire 22. In an example, the engagement feature 28 can comprise one or more threads such that the drive-in screw 24 can be rotatably driven into the bone.

As depicted in FIGS. 6A-B, the suture 20 can be inserted through the channel 26 of the drive-in screw 24 into the distal bone portion 12. The suture 20 can be secured to the distal bone mass 12. In an example, the guide wire 22 can be inserted through the distal bone mass 12 to form a distal opening 15 in the distal bone mass 12 as depicted in FIGS. 6A-B and 9A-B. In this configuration, the suture 20 can extend through the distal opening 15 knotted or expanded to prevent withdrawal of the suture 20 when the suture 20 is tensioned.

As depicted in FIGS. 9A-B, the suture 20 can be tensioned to draw the distal bone mass 12 against the proximal bone mass 10. In an example, the guide wire 22 can be angled such that the tensioned suture 20 applies a pull force along an axis optimal to retaining the proximal bone mass 10 to the distal bone mass 12. The suture 20 can be secured to a tie-off feature 30 mounted on the proximal bone mass 10 such as depicted in FIGS. 6A-6B.

Figure 10:
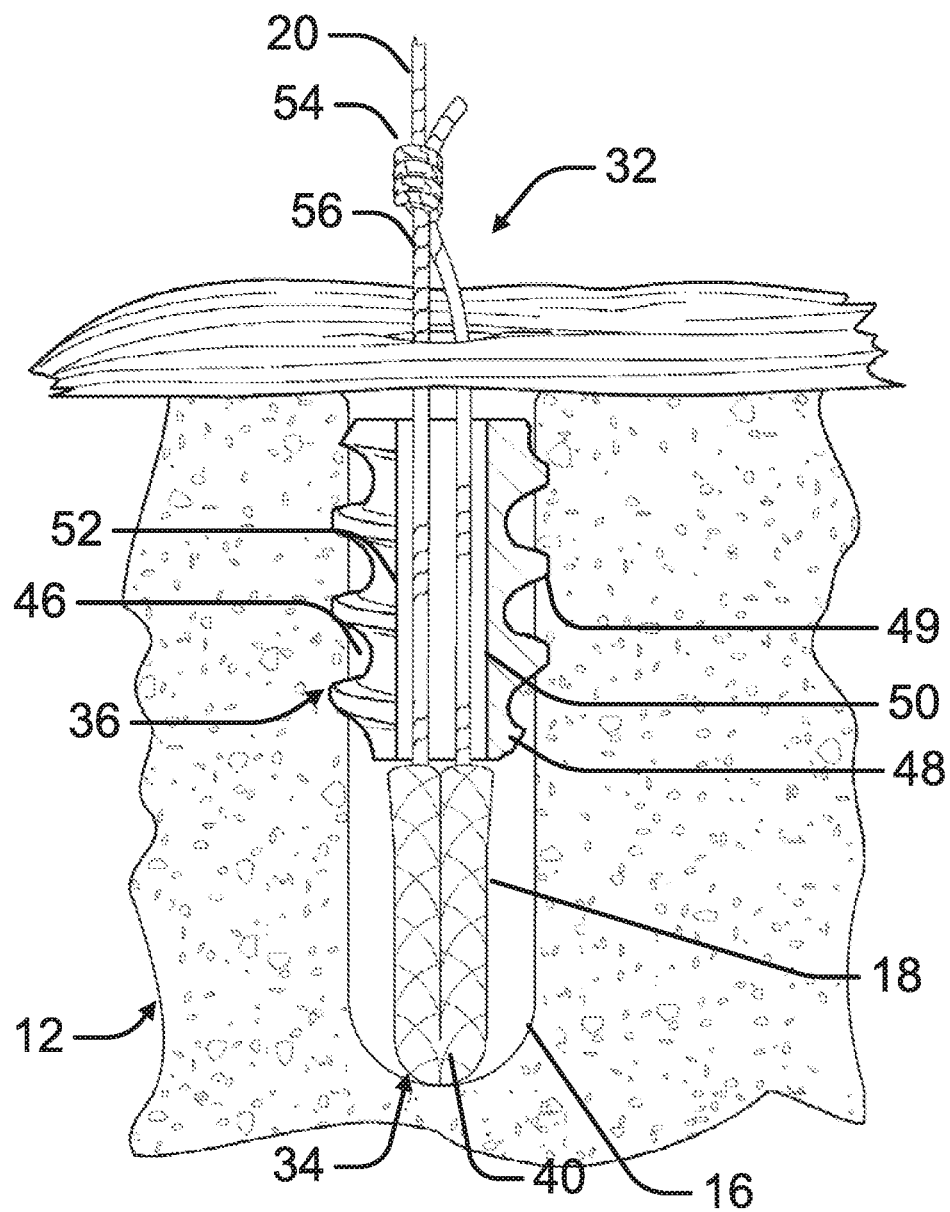
FIG. 10 is across-sectional side view of an anchor system having a nose portion and a tail portion, the anchor system being positioned within a bore hole in a bone prior to deployment of the nose portion, in accordance with at least one example of the present disclosure.
Figure 11:
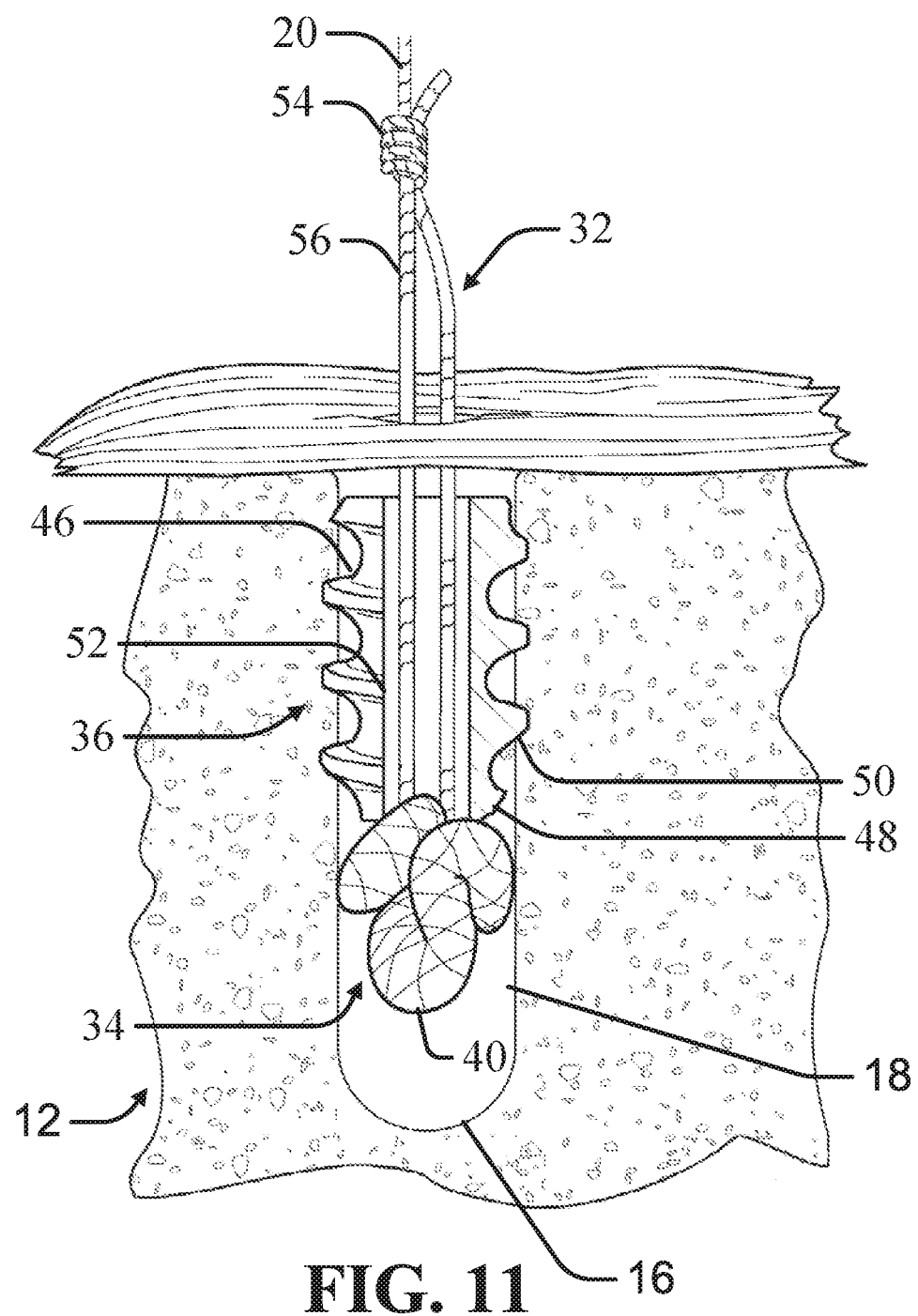
FIG. 11 is a cross-sectional side view of the anchor system depicted in FIG. 10 with the nose portion deployed within the bore hole to engage an inner surface of the bore hole, in accordance with at least one example of the present disclosure.

As depicted in FIGS. 10-11, a suture anchor system 32, according to an example of the present disclosure, can be used to secure the suture 20 to the distal bone mass 12. The suture anchor system 32 can include a nose portion 34 and a tail portion 36. The anchor system 32 can be configured to engage an inner surface 18 of a bore hole 16 formed in a bone to provide an anchor point for a suture 20. The tail portion 36 can be sized to engage the inner surface 18 of the bore hole 16 and fix the tail portion 36 within the bore hole 16. The suture 20 can be threaded through the tail portion 36 to operably engage the nose portion 34 such that the suture 20 can be tensioned to radially expand the nose portion 34 against the inner surface 18. The tensioning of the suture 20 can move the nose portion 34 axially toward the tail portion 36 where the tail portion 36 acts as a back stop preventing the nose portion 34 from being withdrawn from the bore hole 16 by the tensioning of the suture 20.

As depicted in FIGS. 10-11, the nose portion 34 can include at least one flexible element 40. The flexible element 40 can comprise resorbable or non-resorbable materials, including a braided suture, sponges and sponge-like perforated materials that are woven/braided from biocompatible materials or fibers, such as, for example, polymer, polyester, polyethylene, cotton, silk, or other natural or synthetic materials. The flexible element 40 can be made of suture material braided from thin filaments into a form that does not include a core filament. The flexible element 40 can have a generally flaccid shape that can be manipulated in different configurations like a piece of string or shoelace, for example. Accordingly, the flexible element 40 can be bent, folded or otherwise manipulated or deformed into various configurations, such as a bent or U-shape configuration; or a substantially straight configuration; or a deformed or bunched-up, puckered configuration, such as a ball-like or bell-like configuration.

As depicted in FIGS. 10-11, the tail portion 36 can include a body 46 having an outer surface 48 and an inner surface 50 defining an internal channel 52. In at least one example, the body 46 can be sized such that the outer surface 48 approximates the diameter of the bore hole 16 such that the outer surface 48 frictionally engages the inner surface 18 of the bore hole 16. The frictional engagement of the outer surface 48 of the body 46 to the inner surface 18 of the bore hole 16 can prevent axial movement of the body 46 within the bore hole 16. In at least one example, the body 46 can include at least one fixation feature 49 positioned on the outer surface 48. The at least one fixation feature 49 can comprise barbed rings, radially deployable features or other fixation features that permit axial insertion of the body 46 into the bore hole 16 before engagement of the inner surface 50. The fixation feature 49 can engage the bone of the inner surface 18 to prevent axial movement of the tail portion 36 within the bore hole 16.

As depicted in FIGS. 10-11, in an example, the suture 20 can be threaded through the internal channel 52 of the tail portion 36 and through each flexible element 40 before returning through the tail portion 36. In this configuration, the suture 20 can be anchored within the distal bone portion 12 rather than tied in an exterior knot.

As depicted in FIGS. 10-11, in an example, the ends of the suture 20 can be connected with a knot 54, such as a slipknot, forming a strand loop 56 passing through the internal channel 52 of the tail portion and the longitudinal bore of each flexible element 40. In at least one example, the knot 54 can be pre-tied. The suture anchor system 32 can be used to fasten any type of ligaments, grafts or sutures, and can be used, for example, for rotator cuff repair for the shoulder, for acromioclavicular (AC) joint reconstruction, for tibial graft fixation, for ACL reconstruction, and generally for fastening tendons or grafts and sutures to tissue, including soft tissue and bone. In many of such shoulder repair procedures, a tendon is secured to the bone with many suture anchors requiring repeated knot-typing. Such knot-tying is cumbersome and time consuming during an arthroscopic procedure, as it is generally performed through an insertion cannula 58 that is used to deliver the suture anchor system 32.

As depicted in FIGS. 12A-D, in an example, a method of anchoring a suture 20 internally within a distal bone portion 12 can include an anchor site preparation step, an insertion step, an initial fixation step and a final fixation step.

Figure 12A:
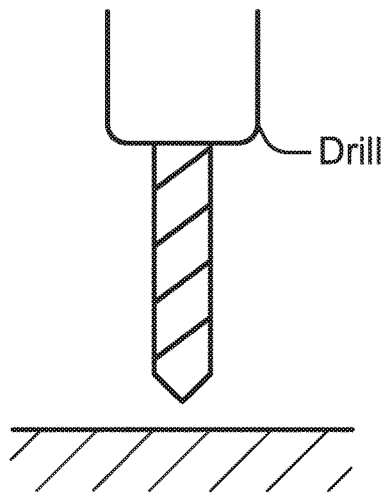
FIG. 12A is a schematic view illustrating preparation of a bore hole in a bone for receiving an anchor system, in accordance with at least one example of the present disclosure.
Figure 12B:
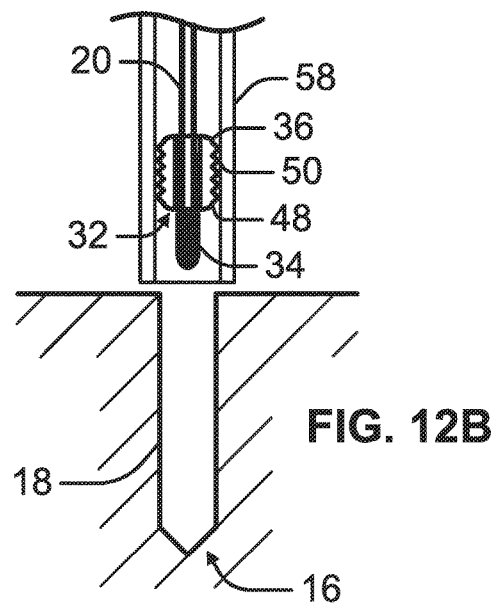
FIG. 12B is a schematic view illustrating positioning the anchor system for insertion within a bore hole, in accordance with at least one example of the present disclosure.

As depicted in FIGS. 12A-B, the anchor site preparation step can include drilling a bore hole 16 in the distal bone portion 12. In at least one example, a hole can be formed in the soft tissue to access the bore hole 16. In at least one example, the bore hole 16 can be drilled through the proximal bone portion 10.

As depicted in FIG. 12B, the insertion step can include delivering the suture anchor system 32 within a cannula 58 to the bore hole 16. The anchor system 32 can be advanced axially, nose portion 34 first, into the bore hole 16. In at least one example, an inner cannula or other tool can extend through the cannula 58 to push the tail portion 36 and corresponding the nose portion 34 into the bore hole 16.

Figure 12C:
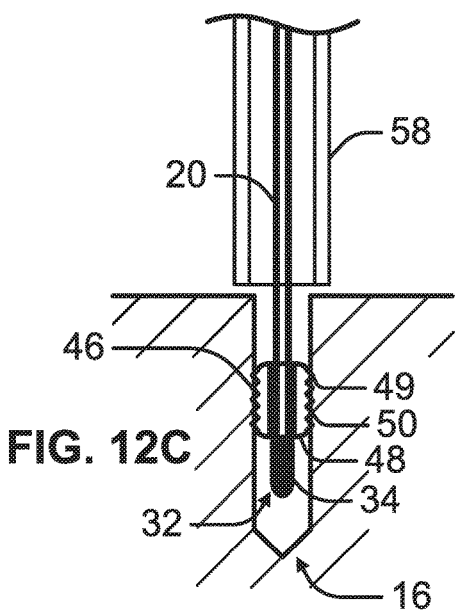
FIG. 12C is a schematic view illustrating insertion of the anchor system within the bore hole and engagement of a tail portion of the anchor system to an inner surface of the bore hole, in accordance with at least one example of the present disclosure.

As depicted in FIG. 12C, the initial fixation step can include fixing the tail portion 36 to the inner surface 18 of the bore hole 16. In an example, the body 46 can be sized such that insertion of the body 46 into the bore hole 16 frictionally engages the outer surface 48 to the inner surface 18 of the bore hole 16 to fix the tail portion 36 within the bore hole 16. In at least one example, the fixation feature 49 positioned on the outer surface 48 can engage the bone defining the inner surface 18 of the bore hole 16 to fix the tail portion 36 within the bore hole 16. In this configuration, the nose portion 34 can be positioned on the interior side of the tail portion 36 such that the tail portion 36 retains the nose portion 34 within the bore hole 16.

Figure 12D:
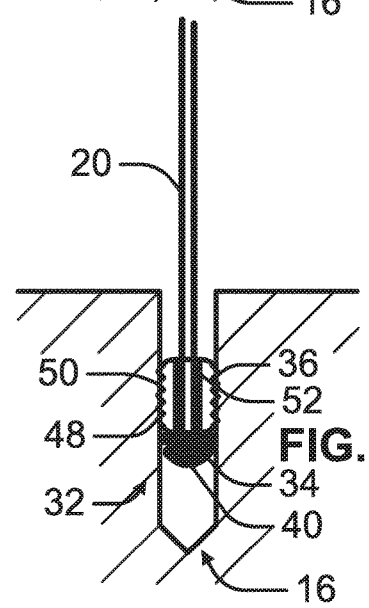
FIG. 12D is a schematic view illustrating deployment of a nose portion of the anchor system to engage the inner surface of the bore hole, in accordance with at least one example of the present disclosure.

As depicted in FIG. 12D, the final fixation step can include tensioning the suture 20 through the internal channel 52 of the tail portion 36 to bunch up the flexible element 40 in a ball or bell-like configuration such that the flexible element 40 extends radially outward such that the flexible element 40 engages the inner surface 18 of the bore hole 16. The suture 20 can be tensioned by pulling the suture 20 away from the tail portion 36. In at least one example, an end of the suture 20 can be pulled away from the knot (not shown) to apply tension of the flexible element 40.

The radial expansion of the flexible element 40 can fix the nose portion 34 within the bore hole 16. The tensioning of the suture 20 can also move the flexible element 40 axially within the bore hole 16 such that the flexible element 40 braces against the tail portion 36. The tail portion 36 can operate as a backstop for the flexible element 40 to prevent the flexible element 40 from being pulled from the bore hole 16 when the suture 20 is tensioned. The tail portion 36 can also facilitate further radial expansion of the flexible element 40 to improve engagement of the flexible element 40 to the inner surface 18 of the bore hole 16. The combined engagement of the nose portion 34 and the tail portion 36 can improve the retention of the anchor system 32 within the bore hole 16.

Various Notes & Examples

Each of these non-limiting examples can stand on its own, or can be combined in any permutation or combination with any one or more of the other examples.

Example 1 is a method of fixing a proximal bone mass to a distal bone mass, comprising: driving a guide wire through the proximal bone mass and the distal bone mass to define a path through the proximal bone mass and the distal bone mass; inserting a suture from the proximal bone mass into the distal bone mass along the path defined by the guide wire; fixing the suture to the distal bone mass; and tensioning the suture to draw the distal bone mass against the proximal bone mass.

In Example 2, the method of Example 1 can optionally include drilling a drive-in screw into at least the proximal bone mass along the path defined by the guide wire.

In Example 3, the method of Example 2 can optionally include that the drive-in screw is driven through the proximal bone mass into the distal bone mass.

In Example 4, the method of any one or more of Examples 2-3 optionally include, wherein the drive-in screw is withdrawn from at least the proximal bone mass following fixation of the suture to the distal bone mass.

In Example 5, the method of any one or more of Examples 2-4 optionally include, wherein the drive-in screw defines a center channel for receiving the suture.

In Example 6, the method of any one or more of Examples 1-5 optionally include, wherein the suture includes an expandable nose portion.

In Example 7, the method of Example 6 optionally includes tensioning the suture when the nose portion is positioned within the distal bone mass to expand the nose portion and fix the suture to the distal bone mass.

In Example 8, the method of any one or more of Examples 6-7 optionally includes inserting the suture through the distal bone mass such that the nose portion protrudes through a distal opening in the distal bone mass formed by the guide wire; and tensioning the suture to expand the nose portion and prevent withdrawal of the suture through the distal opening thereby fixing the suture to the distal bone mass.

In Example 9, the method of any one or more of Examples 7-8 optionally includes that the suture includes a tail portion having engagement features engagable to a bone surface of at least one of the distal bone mass and proximal bone mass.

In Example 10, the method of Example 9 optionally includes fixing the tail portion within at least the distal bone mass; wherein tensioning the suture draws the nose portion against the tail portion to facilitate expansion of the nose portion against the distal bone portion.

In Example 11, the method of any one or more of Examples 1-10 optionally includes that the proximal bone mass is larger than the distal bone mass.

Example 12 is a system for fixing a proximal bone mass to a distal bone mass, comprising: a guide wire configured to be driven through the proximal bone mass and the distal bone mass to define a path through the proximal bone mass and the distal bone mass; and a suture insertable through the proximal bone mass into the distal bone mass along the path defined by the guide wire; wherein the suture is configured to be fixed to the distal bone mass and tensioned to draw the distal bone mass against the proximal bone mass.

In Example 13, the system of Example 12 optionally includes a drive-in screw defining a center channel for receiving the suture and configured to be drilled into at least the proximal bone mass along the patent defined by the guide wire.

In Example 14, the system of Example 13 optionally includes that the drive-in screw is driven through the proximal bone mass into the distal bone mass.

In Example 15, the system of any one or more of Examples 13-14 optionally includes that the drive-in screw is configured to be withdrawn from at least the proximal bone mass following fixation of the suture to the distal bone mass.

In Example 16, the system of any one or more of Examples 12-15 optionally includes that the suture further comprises: a nose portion configured to expand radially when the suture is tensioned.

In Example 17, the system of Example 16 optionally includes that the suture further comprises: a tail portion having engagement features engagable to a bone surface of at least one of the distal bone mass and proximal bone mass; wherein the tail portion is configured to engage the bone surface to fix the tail portion in at least within the distal bone mass such that the suture can be tensioned to draw the nose portion against the tail portion to facilitate expansion of the nose portion against the distal bone portion.

In Example 18, the system of any one or more of Examples 12-17 optionally includes that the proximal bone mass is larger than the distal bone mass.

Example 19 is a system for fixing a proximal bone mass to a distal bone mass, comprising: a guide wire configured to be driven through the proximal bone mass and the distal bone mass to define a path through the proximal bone mass and the distal bone mass; and a suture insertable through the proximal bone mass into the distal bone mass along the path defined by the guide wire, the suture comprising: a nose portion configured to expand radially when the suture is tensioned, and a tail portion having one or more engagement features engagable to a bone surface of at least one of the distal bone mass and proximal bone mass, wherein the tail portion is configured to engage the bone surface to fix the tail portion within at least the distal bone mass such that the suture can be tensioned to draw the nose portion against the tail portion to facilitate expansion of the nose portion against the distal bone mass.

In Example 20, the system of Example 19 optionally includes that the tail portion comprises: a drive-in screw defining a center channel for receiving the suture and configured to be drilled into at least the proximal bone mass along the path defined by the guide wire.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A system for fixing a proximal bone mass to a distal bone mass, comprising:
   a guide wire configured to be driven through the proximal bone mass and the distal bone mass to define a path through the proximal bone mass and the distal bone mass;
   a suture insertable through the proximal bone mass into the distal bone mass along the path defined by the guide wire, the suture including a radially expandable nose portion; and
   a drive-in screw defining a center channel for receiving the suture and configured to be drilled into at least the proximal bone mass along the path defined by the guide wire, the center channel extending from a proximal opening in a proximal end of the drive-in screw to a distal opening in a distal end of the drive-in screw;
   wherein the suture is configured to extend through the center channel such that the nose portion is positionable adjacent to the distal opening;
   wherein the suture is configured to be fixed to the distal bone mass and tensioned to draw the distal bone mass against the proximal bone mass; and
   wherein the nose portion is configured to expand radially against the distal end of the drive-in screw when the suture is tensioned.

2. The system of claim 1, wherein the drive-in screw is sized to be driven through the proximal bone mass into the distal bone mass.

3. The system of claim 1, wherein the drive-in screw is configured to releasably engage surrounding bone along the path such that the drive-in screw can be withdrawn from at least the proximal bone mass following fixation of the suture to the distal bone mass.

4. The system of claim 1, wherein the
   drive-in screw comprises one or more engagement features engagable to a bone surface of at least the distal bone mass.

5. The system of claim 4, wherein the suture includes a knot that forms a strand loop configured to pass through an interior channel of the tail portion.

6. The system of claim 1, wherein the proximal bone mass is larger than the distal bone mass.

7. The system of claim 1, the drive-in screw further comprising a threaded engagement feature for engaging an inner wall of the path formed by the guide wire.

8. The system of claim 1, wherein the suture is configured to be expanded to a radial diameter greater than an inner diameter of the center channel of the drive-in screw to prevent the suture from being withdrawn through the center channel.

9. The system of claim 1, wherein the drive-in screw comprises a first drive-in screw, and further comprising:
   a second drive-in screw configured to be inserted into the path behind the first drive-in screw such that a second center channel of the second drive-in screw aligns with the first center channel of the first drive-in screw.

10. A system for fixing a proximal bone mass to a distal bone mass, comprising:
    a guide wire configured to be driven through the proximal bone mass and the distal bone mass to define a path through the proximal bone mass and the distal bone mass;
    a suture insertable through the proximal bone mass into the distal bone mass along the path defined by the guide wire, wherein an end of the suture is tied back to a center portion of the suture with a slip knot to form a strand loop;
    a nose portion configured to expand radially when the suture is tensioned, the nose portion comprising a flexible element; and
    a tail portion having one or more engagement features engagable to a bone surface of at least one of the distal bone mass and proximal bone mass, the tail portion defining an internal channel configured for passing at least one of the guide wire and the suture longitudinally through the tail portion;
    wherein the tail portion is configured to engage the bone surface to fix the tail portion within at least the distal bone mass such that the suture can be tensioned to draw and deform the flexible element of the nose portion against the tail portion to facilitate radial expansion of the nose portion against the distal bone mass, and wherein tensioning the suture pulls the strand loop closed.

11. The system of claim 10, wherein the tail portion comprises:
a drive-in screw configured to be drilled into at least the proximal bone mass along the path defined by the guide wire.

12. The system of claim 10, wherein the engagement feature of the tail portion comprises a threaded engagement feature for engaging the bone surface.

13. The system of claim 10, wherein the nose portion is radially expandable to a radial diameter greater than an inner diameter of the internal channel of the tail portion to prevent the suture from being withdrawn through the internal channel of the tail portion.

14. The system of claim 10, wherein the strand loop is threaded through the flexible element;
wherein tensioning the suture to pull the strand loop closed deforms the flexible element against the tail portion.

15. The system of claim 14, wherein the flexible element comprises a bent configuration prior to tensioning of the suture.

16. A system for fixing a proximal bone mass to a distal bone mass, comprising:
a guide wire configured to be driven through the proximal bone mass and the distal bone mass to define a path through the proximal bone mass and the distal bone mass;
a suture insertable through the proximal bone mass into the distal bone mass along the path defined by the guide wire;
a first drive-in screw defining a first center channel for receiving the suture and configured to be drilled into at least the proximal bone mass along the path defined by the guide wire; and
a second drive-in screw configured to be inserted into the path behind the first drive-in screw such that a second center channel of the second drive-in screw aligns with the first center channel of the first drive-in screw;
wherein the suture is configured to be fixed to the distal bone mass and tensioned to draw the distal bone mass against the proximal bone mass.

* * * * *